United States Patent [19]

Neumiller et al.

[11] Patent Number: 4,793,864
[45] Date of Patent: Dec. 27, 1988

[54] SUBSTRATE HAVING AN ADHERENT PHOTO-PRODUCT COATING ON ITS SURFACE AND A METHOD OF COATING SAID SUBSTRATE

[75] Inventors: Phillip J. Neumiller; Robert M. Etter, both of Racine, Wis.

[73] Assignee: S. C. Johnson & Son, Inc., Racine, Wis.

[21] Appl. No.: 49,062

[22] Filed: May 12, 1987

Related U.S. Application Data

[63] Continuation-in-part of Ser. No. 3,350, Jan. 14, 1987.

[51] Int. Cl.$^4$ .......................... B08B 3/00; C08F 2/48; C08G 2/16
[52] U.S. Cl. .......................................... 134/1; 134/26; 204/157.75; 427/53.1; 428/426; 428/432; 428/469; 428/524; 522/173; 522/178; 528/126; 528/128
[58] Field of Search .................. 522/173, 178; 528/126, 528/128; 204/157.75; 428/426, 432, 524; 427/53.1; 63/32; 134/38, 39, 40, 25.4, 26, 1

[56] References Cited

U.S. PATENT DOCUMENTS

| | | | |
|---|---|---|---|
| 1,962,132 | 6/1934 | Bradshaw | 106/173.1 |
| 2,639,290 | 5/1953 | Mahler | 556/110 |
| 2,686,812 | 8/1954 | Wynn et al. | 568/322 |
| 2,693,492 | 11/1954 | Hoch | 106/187 |
| 2,773,778 | 12/1956 | Hoch et al. | 252/589 |
| 2,876,210 | 3/1959 | Wynn et al. | 252/404 |
| 2,989,416 | 6/1961 | Standish | 428/263 |
| 3,043,709 | 7/1962 | Amborski | 428/216 |
| 3,049,443 | 8/1962 | Coleman | 8/527 |
| 3,098,863 | 7/1963 | Dessauer et al. | 556/150 |
| 3,100,716 | 8/1963 | Kibler et al. | 106/187 |
| 3,206,428 | 9/1965 | Stanley | 524/241 |
| 3,216,969 | 11/1965 | Cyba | 524/204 |
| 3,296,191 | 1/1967 | Smallwood | 524/328 |
| 3,361,709 | 1/1968 | Brown | 524/328 |
| 3,413,263 | 11/1968 | Strobel | 524/328 |
| 3,448,133 | 6/1969 | Strobel | 524/328 |
| 3,460,960 | 8/1969 | Francel et al. | 428/336 |
| 3,464,953 | 9/1969 | Newland | 524/202 |
| 3,616,367 | 10/1971 | Zunker | 522/21 |
| 3,642,690 | 2/1972 | Mills | 524/100 |
| 3,755,450 | 8/1973 | Anderson | 568/304 |
| 3,772,354 | 11/1973 | Fredricks | 556/45 |
| 3,786,021 | 1/1974 | Mathis | 524/204 |
| 3,871,901 | 3/1975 | Carlsson | 428/220 |
| 3,997,464 | 12/1976 | Tucker | 252/588 |
| 3,998,752 | 12/1976 | Haacke | 556/150 |
| 4,029,684 | 6/1977 | Avar et al. | 556/150 |
| 4,097,454 | 6/1978 | Tozzi et al. | 524/302 |
| 4,228,066 | 10/1980 | Johnson | 524/162 |

OTHER PUBLICATIONS

BASF Wyandotte Corporation Technical Data, "UNIMAL UV Absorbers, for Cosmetics, Plastics, Coatings, Textiles".

Primary Examiner—John C. Bleutge
Assistant Examiner—David Buttner

[57] ABSTRACT

This invention relates to a natural or synthetic gemstone or mineral substrate having on its surface an adherent photo-product coating, and a method for coating that substrate, which coating is formed by exposing to light in the presence of an oxygen source, a reactant mixture comprising: 2,2′4,4′-tetrahydroxybenzophenone, with (1) ammonium hydroxide and optionally a trace amount of at least one reactive metal, or (2) ammonium hydroxide and at least one metal salt, or (3) at least one metal salt and at least one amine, or (4) ammonium hydroxide, at least one metal salt and at least one amine; in a suitable solvent.

52 Claims, 3 Drawing Sheets

SUBSTRATE HAVING AN ADHERENT PHOTO-PRODUCT COATING ON ITS SURFACE AND A METHOD OF COATING SAID SUBSTRATE

This application is a continuation-in-part of commonly assigned, co-pending application, Ser. No. 003,350, filed on 01-14-87, entitled "A Photo-Product Energy Barrier Composition".

The present invention relates to a substrate having an adherent photo-product coating and a method for coating a substrate with that photo-product composition. More particularly, it relates to a photo-product coating adhered to the surface of a natural or synthetic gemstone or mineral substrate, and a method for producing such a structure by coating a substrate with a substituted benzophenone reactant mixture which is exposed to light in the presence of an oxygen source.

It has long been desired to provide a substrate and coating which provides an effective screen against ultraviolet and infrared radiation. Such a coating can be applied to windows, eyeglasses, lighting fixtures, computer monitor screens, and other similar substrates to protect them and possibly their users from such radiation. Additionally, the coating can be used either to change the aesthetics of gemstone and mineral substrates or when these substrates are used as detectors and/or sensors, to change their optical, electromagnetic transmission and electronic properties. Conventional films typically lack the desired absorption and adherency characteristics to accomplish these objectives.

Benzophenones and substituted benzophenones are well known as ultraviolet light absorbers. See for example, BASF Wyandotte Corporation's Technical Data entitled "UVIMUL UV Absorbers, For Cosmetics, Plastics, Coatings, Textiles", which discloses numerous substituted benzophenones, and 2,2',4,4'-tetrahydroxybenzophenone in particular, as useful absorbers of ultraviolet light for a variety of applications. Additionally, Smallwood et al., U.S. Pat. No. 3,296,191, discloses that thermally-produced nickel or cobalt derivatives of specified hydroxybenzophenones, which do not include 2,2',4,4'-tetrahydroxybenzophenone, are useful as light and heat stabilizers for polypropylenes The disclosed benzophenones are 2,2'-dihydroxy-4-alkoxybenzophenones with $C_6$–$C_{20}$ alkyl radicals being required for effective stabilization. Additionally, the coordination complex contains no more than about one mole of metal for every two moles of benzophenone.

U.S. Pat. No. 2,989,416 to Standish, however, states that these materials, in general, are not entirely satisfactory because of the difficulty in applying them to surfaces and the relative ease by which they are washed from such surfaces. Standish addresses such problems by reacting certain ortho-hydroxyl substituted benzophenones, with a trivalent metal, either chromium or aluminum, in molar ratios of benzophenone to metal ranging from 1:0.5 to 1:10 to form water-soluble Werner complexes that absorb longer wavelength ultraviolet radiation. The Standish product is a thermally produced compound, not a composition produced by a photoreaction.

It is an object of this invention to provide a photo-product coating composition that significantly reduces the transmission of electromagnetic radiation.

More specifically, it is an object of this invention to provide a natural or synthetic gemstone or mineral substrate having on its surface an adherent photo-product coating.

Still more specifically, it is an object of this invention to provide a photo-product coating that strongly adheres to natural and synthetic gemstone and mineral substrates, including glass, sapphire, quartz, ruby, peridot, diamond, emerald, zircon, gallium arsenide, garnet and the like.

Additionally, it is an object of this invention to provide a method of cleaning natural and synthetic gemstone and mineral substrates by applying and then removing this photo-product coating.

These and additional objectives are shown from the description below.

SUMMARY OF THE INVENTION

In the substrate embodiment, this invention consists of a natural or synthetic gemstone or mineral substrate having on its surface an adherent photo-product coating, which coating is formed by exposing to light in the presence of an oxygen source, a reactant mixture ("Reactant Mixture I") comprising (a) 2,2',4,4'-tetrahydroxybenzophenone, (b) ammonium hydroxide, and (c) optionally a trace amount of at least one reactive metal, in a solvent.

In a further substrate embodiment, the reactant mixture ("Reactant Mixture II") comprises (a) 2,2'4,4'-tetrahydroxybenzophenone, (b) ammonium hydroxide, and (c) at least one metal salt, in a solvent.

In still another substrate embodiment, the reactant mixture ("Reactant Mixture III") comprises (a) 2,2',4,4'-tetrahydroxybenzophenone, (b) at least one metal salt, and (c) at least one amine, in a solvent.

In still a further substrate embodiment, the reactant mixture ("Reactant Mixture IV") comprises (a) 2,2',4,4'-tetrahydroxybenzophenone, (b) ammonium hydroxide, (c) at least one metal salt, and (d) at least one amine, in a solvent.

In the method embodiment, this invention consists of a method of forming an adherent photo-product coating on the surface of a natural or synthetic gemstone or mineral substrate comprising the steps of (1) preparing a reactant mixture comprising (a) 2,2',4,4'-tetrahydroxybenzophenone, (b) ammonium hydroxide, and (c) optionally a trace amount of at least one reactive metal, in a solvent; (2) contacting said substrate with said reactant mixture; and (3) exposing said reactant mixture in contact with said substrate to light in the presence of an oxygen source. ("Method of Reactant Mixture I").

In another method embodiment, the reactant mixture comprises (a) 2,2'4,4'-tetrahydroxybenzophenone, (b) ammonium hydroxide, and (c) at least one metal salt, in a solvent. ("Method of Reactant Mixture II").

In still another method embodiment, the reactant mixture comprises (a) 2,2',4,4'-tetrahydroxybenzophenone, (b) at least one metal salt, and (c) at least one amine, in a solvent. ("Method of Reactant Mixture III").

In still a further method embodiment, the reactant mixture comprises (a) 2,2',4,4'-tetrahydroxybenzophenone, (b) ammonium hydroxide, (c) at least one metal salt, and (d) at least one amine, in a solvent. ("Method of Reactant Mixture IV").

In the method of cleaning embodiment, this invention consists of a method of cleaning a natural or synthetic gemstone or mineral substrate comprising the steps of (A) forming an adherent photo-product coating on the surface of said substrate by (1) preparing any of the above I-IV reactant mixtures; (2) contacting said substrate with the reactant mixture; and (3) exposing the reactant mixture in contact with said substrate to light in the presence of an oxygen source; and then (B) removing said photo-product coating from the surface of said substrate.

It has been surprisingly found that 2,2',4,4'-tetrahydroxybenzophenone (THBP) in combination with (1) ammonium hydroxide, or (2) ammonium hydroxide and at least one metal salt, or (3) at least one metal salt and at least one amine, or (4) ammonium hydroxide, at least one metal salt and at least one amine; in a suitable solvent, produces an adherent photo-product coating on the surface of a natural or synthetic gemstone or mineral substrate upon exposure to light in the presence of oxygen. On glass substrates, this photo-product coating significantly reduces the transmission of electromagnetic radiation by reflecting infrared radiation in the range of about 800 to 15,000 nanometers and absorbing ultraviolet radiation in the range of about 200 to 400 nanometers. Additionally, the coating can be used to change the aesthetics of a gemstone or mineral substrate or when the substrate is used as a detector and/or sensor, to change its optical, electromagnetic transmission and/or electronic properties.

It has been additionally found that the photo-product coatings of this invention tenaciously adhere to many substrates, including glass, quartz, gallium arsenide, sappiire, ruby, peridot, diamond, emerald, zircon, garnet and the like and are insoluble in water and many organic solvents and therefore resist removal from these substrates once applied.

DETAILED DESCRIPTION OF THE INVENTION

Figure 1:
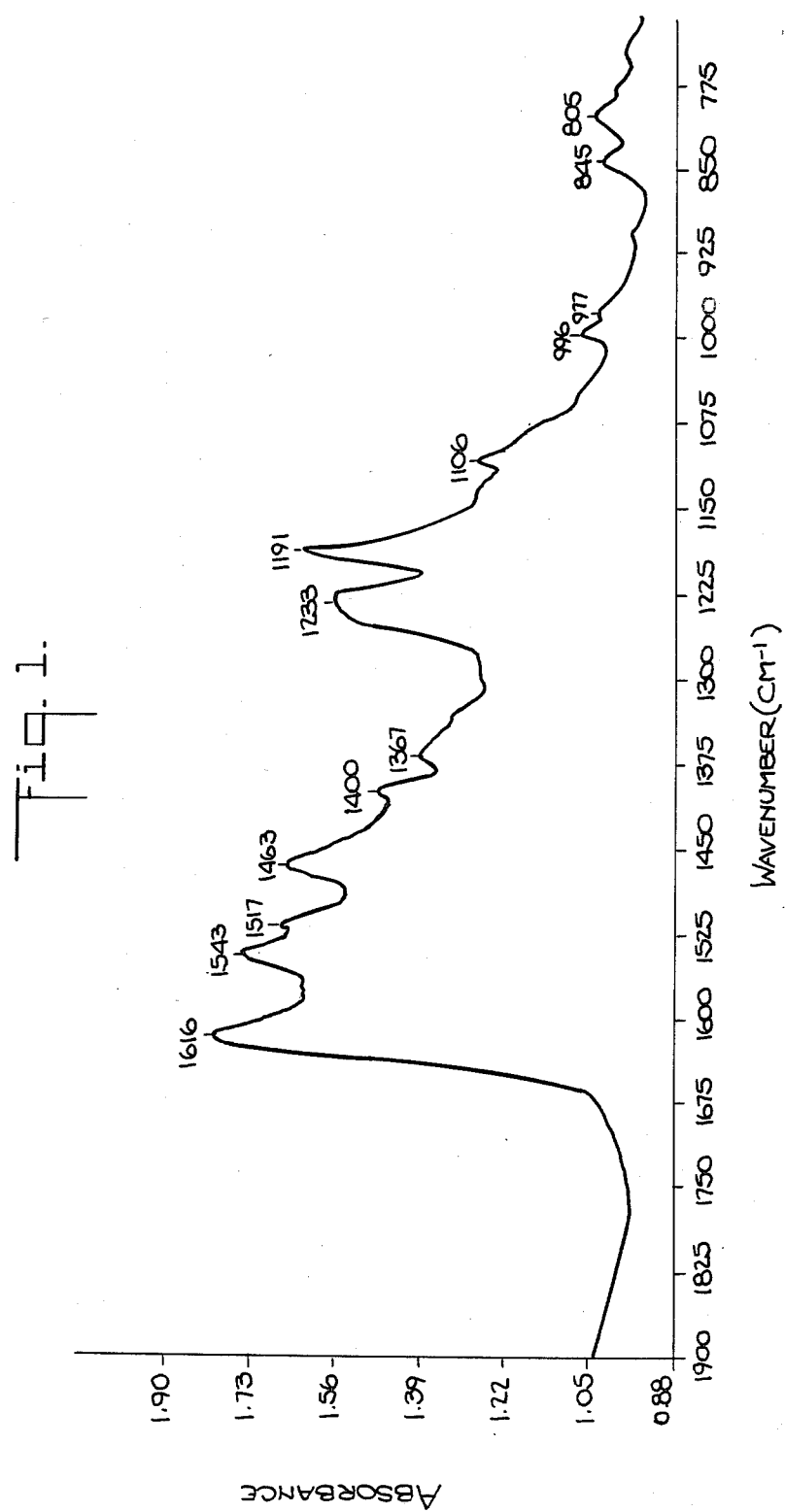
FIG. 1 is the infrared absorption spectrum for the photo-product coating of claim 21.

In one substrate embodiment, the invention consists of a natural or synthetic gemstone or mineral substrate having on its surface an adherent photo-product coating, which coating is formed by exposing to light in the presence of an oxygen source, a reactant mixture ("Reactant Mixture I") comprising (a) 2,2',4,4'-tetrahydroxybenzophenone; (b) ammonium hydroxide; and (c) optionally a trace amount of at least one reactive metal; in a solvent.

Additionally, the method of forming an adherent photo product coating on the surface of a natural or synthetic gemstone or mineral substrate comprising the steps of (1) preparing Reactant Mixture I in a solvent; (2) contacting said substrate with said reactant mixture; and (3) exposing said reactant mixture in contact with said substrate to light in the presence of an oxygen source; is within the scope of this invention.

In this and other more preferred embodiments of this invention, the benzophenone found best to meet the objectives of this invention and provide a photo-product coating is 2,2'4,4'-tetrahydroxybenzophenone. Other benzophenones that do not yield the present photo-product coating include 2,2'-dihydroxybenzophenone; 2,2'-dihydroxy-4,4'-dimethoxybenzophenone; 4,4'-dihydroxybenzophenone; and 2,4'-dihydroxybenzophenone. These particular benzophenones were tested by the Method of Reactant Mixture IV and found to give various precipitants without producing a photo-product coating of this invention.

Additionally, certain sources of ammonium ion ($NH_4+$) and hydroxyl ion ($-OH$) other than ammonium hydroxide have not proven effective in producing the photo-product coating of this invention. For example, benzyltrimethyl ammonium hydroxide, tetramethyl ammonium hydroxide, ammonium bromide and ammonium acetate, all failed to produce the requisite photo-product coating when utilized as substitutes for ammonium hydroxide in the Method of Reactant Mixture IV.

The reactive metal can be employed in elemental form or as an organic or inorganic compound, providing that it is capable of reacting with the solvated, ammoniated THBP. It is postulated that the reactive metal in its cationic form promotes formation of a stable photo-product. In certain cases, elemental metal, such as nickel, can be employed in powder form or the like. Such forms are adapted to be readily solubilized as an hydroxide or oxide. For most purposes, however, metal organoates or metal inorganic salts are preferred.

In the Method of Reactant Mixture I, a reactive metal need not be added to the mixture of reactants. X-ray analysis, however, has shown that when combining THBP and ammonium hydroxide in the presence of a solvent, trace amounts of reactive metals, in particular, zinc, are typically present as contaminants.

It is believed that the reactive metal assists in forming and stabilizing the photo-product. In the other reactant mixtures (mixtures II, III and IV), at least one metal salt is intentionally added to the mixture of reactants. Useful reactive metals, especially metal salts are provided hereafter in connection with the discussion of Reactant Mixture II.

The concentration of THBP and ammonium hydroxide utilized in accordance with this aspect of the invention varies from a molar ratio of 1:1 to about 20:1, with a molar ratio of 18 moles of THBP to about 5 moles of ammonium hydroxide being preferred.

The reaction is typically carried out at room temperature (approximately 22° C.). The reaction temperature is not critical, and the addition of heat is not necessary, nor is it a limiting factor in the photo-product reaction. However, with some of the other reaction product formulas a heat treatment may be necessary to promote the solubilization of the reactants.

The photo-reaction is carried out in the presence of light, such as sunlight or artificially produced ultraviolet radiation in the range of about 200 to 400 nanometers, with about 340 to 360 nanometers being preferred. The more intense the light, particularly light in the 340 to 360 nanometer range, the more rapid the formation of the photo-product. Artificial light in this range, e.g., light produced by a mercury arc lamp, enhances the rate of photo-product formation and can, under certain circumstances, provide a visible coating in a few hours. Additionally, this photo-product coating adheres less tenaciously to various substrates as compared with those of Reactant Mixtures II and IV. The coating of Reactant Mixture I is also dissolved by dimethyl formamide.

A visible photo-product coating of Reactant Mixture I forms slowly on the sides of a glass vial or on a glass substrate. While the photo-product can be detected almost instantly upon mixing the reactants under the proper conditions, it usually takes between about 2 and 3 days of exposure of Reactant Mixture I to direct sunlight before a film becomes noticeable to the naked eye.

According to this invention, photo-product coatings can be made by effecting contact of the substrate and the reactant mixture in a solvent. It is necessary only that the reaction medium be such that each of the reactants are soluble in it. Water alone can be utilized, but does not impart sufficient solubility to yield optimum results. Other suitable solvents are alcohols, with preferred solvents including lower alkanols, such as ethanol, isopropanol, n-propanol, isobutanol, n-butanol, and the like. Aqueous alcohol solvents and various mixtures of these solvents can also be utilized.

An oxygen source within the scope of this invention is molecular oxygen. Air contains sufficient oxygen to meet the objectives of this invention. Generally, sufficient dissolved oxygen will be present if the surface of the reactant mixture is exposed to a source of gaseous oxygen. It has been observed that bubbling pure molecular oxygen through the reactant mixture speeds up the reaction rate. Other oxygen sources providing molecular oxygen may also be employed. The photo product coating will not, however, form in the absence of oxygen. For example, Reactant Mixture IV, under a nitrogen or argon atmosphere in the absence of oxygen, did not produce a photo-product coating of the present invention.

The substrates that can be utilized in accordance with the teachings of this invention include natural and synthetic gemstones and minerals. In general, substrates that exhibit at least some light transmittance are included. The natural and synthetic gemstone substrates include sapphire, ruby, peridot, diamond, emerald, zircon, garnet and the like. The natural and synthetic mineral substrates include glass, quartz, gallium arsenide, and amorphous, polycrystalline and/or crystalline hydrogenated silicon and the like. The term glass is intended to include an amorphous, inorganic, translucent or transparent substance, generally a silicate, borate and/or phosphate, formed by fusion of a form of silica or by fusion of oxides of boron or phosphorous with a flux (potash) and stabilizer (lime, alumina). All types of glass, for example, soda-lime (float) glass, polished glass, potash glass, borosilicate glass, barium crown glass, quartz glass, pyrex glass, and other like transparent, opaque or colored glass can be employed. This term is also intended to cover glass or optical fibers, including vapor-deposited optical fibers. The invention is not intended to be limited by the substrate material.

The substrate can be of any suitable geometrical shape or size, including planar, spherical, toroidal, rod-shaped, block-shaped or the like. The substrate can be machined into any product, such as a lens, a tube, a plate or the like. The substrate can form an integral part of a window, a lighting fixture, a monitor screen, a detector, a sensor, a solar cell, eyeglasses, a light absorbent or a light transmissive coat for an object useful in space and the like.

FIG. 1 shows the infrared absorption spectrum of one particular Reactant Mixture I photo-product coating formed by exposure to fluorescent light in the presence of air for 5 days. The reactant mixture contained 1% ammonium hydroxide, 4% THBP and 95% ethanol Trace amounts of zinc were detected in this photo-product by x-ray analysis. The infrared absorption spectrum of FIG. 1 was determined by placing a silver chloride plate in the above mixture, and leaving the plate and reactant mixture exposed to fluorescent light in a laboratory for 5 days in a normal atmospheric environment. After 5 days, the plate was removed, washed with ethanol, then washed with acetone, dried and placed into an FTIR instrument (a Nicolet model 60SX Fourier Transform Infrared Spectrometer).

In another substrate embodiment, this invention consists of a natural or synthetic gemstone or mineral substrate having on its surface an adherent photo product coating, which coating is formed by exposing to light in the presence of an oxygen source, a reactant mixture comprising (a) 2,2'4,4'-tetrahydroxybenzophenone; (b) ammonium hydroxide; and (c) at least one metal salt; in a solvent. Additionally, the Reactant Mixture II method of forming an adherent photo-product coating on the surface of a natural or synthetic gemstone or mineral substrate is also within the scope of this invention.

The metal salts that can be utilized in accordance with this aspect of the invention include the metal cations zinc, cadmium, copper, silver, nickel, zirconium, palladium, platinum, cobalt, rhodium, iron, ruthenium, manganese, tin, lead, polonium, mercury, and the like, and mixtures thereof, in combination with various inorganic and organic anions, such as sulfate, nitrate, bromide, chloride, acetate, formate, benzosulfonate, benzoate, and carbonate, and the like, and mixtures thereof. The preferred metal salts include nickel chloride ($NiCl_2$ $6H_2O$), cobalt chloride, silver acetate, copper chloride, iron chloride, zinc acetate, lead chloride and copper acetate.

The concentrations of the three reactants used to form Reactant Mixture II are as follows: THBP from about 0.01% to 10%, ammonium hydroxide from about 0.01 to 10%, and metal salt from about 0.001 to 5%. All weight percents are based on the weight of the total composition.

A preferred product is formed from a ratio of at least about 18 moles of THBP, 5 moles of ammonium hydroxide, and 1 mole of a metal salt, such as nickel chloride. The maximum concentration of reactants in the process, especially THBP, is limited by solubility.

The reaction conditions described above for Reactant Mixture I apply to Reactant Mixture II, except that the photo-product reaction proceeds at a faster rate. A noticeable film is usually observed within 24 hours upon exposure to sunlight in the presence of oxygen. It is postulated that the addition of the metal salt permits the formation of an intermediate metal-ligand-coordination complex which improves both the energy barrier properties of the Substrate of Reactant Mixture II and the rate of reaction.

The rate of reaction is, as previously explained, dependent on the type and intensity of light. However, the rate of reactivity is, in general, also dependent on the metal cation utilized, with the general order of reactivity as follows: manganese ($Mn^{+2}$), ruthenium ($Ru^{+2}$), iron ($Fe^{+2}$), rhodium ($Rh^{+2}$), cobalt ($Co^{+2}$), platinum ($Pt^{+2}$), palladium ($Pd^{+2}$), copper ($Cu^{+2}$), lead ($Pb^{+2}$), nickel ($Ni^{+2}$), cadmium ($Cd^{+2}$), and zinc ($Zn^{+2}$).

The photo-product coating of Reactant Mixture II is evidenced by the formation of a film with a metallic appearance which forms on the substrate that is in contact with the reactants. For example, if the reactants are mixed in a glass vial, the photo product will form and tenaciously adhere to the glass substrate upon exposure to light in the presence of oxygen.

This invention, in another substrate aspect, consists of a natural or synthetic gemstone or mineral substrate having on its surface an adherent photo-product coating, which coating is formed by exposing to light in the presence of an oxygen source, a reactant mixture comprising (a) 2,2',4,4'-tetrahydroxybenzophenone; (b) at least one metal salt; and (c) at least one amine; in a solvent. Additionally, the Reactant Mixture III method of forming an adherent photo-product coating on the surface of a natural or synthetic gemstone or mineral substrate is within the scope of this invention.

The amines that are used in accordance with this invention include triethanolamine, monomethanolamine, ethanolamine, diethanolamine, butylamine, n-amylamine, and the like. In the absence of ammonium hydroxide, it is believed that the amine's sole function, in particular the preferred amine, triethanolamine, is assisting in the deprotonation of THBP prior to the photo-reaction. Regardless of the presence or absence of ammonium hddroxide, however, the amines mentioned above, including others, also have the capacity to form an amine-metal coordination complex, which is believed to complex with the deprotonated THBP during the process. Additionally, the amine-metal complex hinders the formation of insoluble metal hydroxides.

Reactant Mixture III can be conveniently utilized in commercial use. However, to inhibit the photo-reaction from occurring prior to application by the user, a stabilized formulation has been developed. In the stabilized formulation, acetic acid or carbonic acid is added to Reactant Mixture III. The pH of this formulation is typically about 6.2±0.2.

Upon application, the acetic acid volatilizes or, if carbonic acid is used, it converts to carbon dioxide and water. This raises the pH thereby allowing the THBP to be slowly deprotonated by the triethanolamine and complexed with the metal-amine. It is believed that the acetic acid or carbonic acid initially stabilizes the THBP and prevents the deprotonation reaction from occurring.

This stabilized photo-product coating initially becomes visible in about 24 hours upon exposure to sunlight in the presence of oxygen and continues reacting for one to two weeks thereafter, producing a fully-developed film within that time period.

The concentration ranges of the three reactants employed in Reactant Mixture III, in accordance with this invention, are as follows: about 0.01 to 10% of THBP, about 0.001 to 5% of at least one metal salt, preferably copper acetate, and about 0.01 to 2% of at least one amine, preferably triethanolamine. The amount of acetic acid or carbonic acid required to prevent deprotonization of THBP is usually the amount requied to lower the pH of the reactant mixture to about 6 or below. Examples of these formulations are given in Table 2 hereafter.

Figure 2:
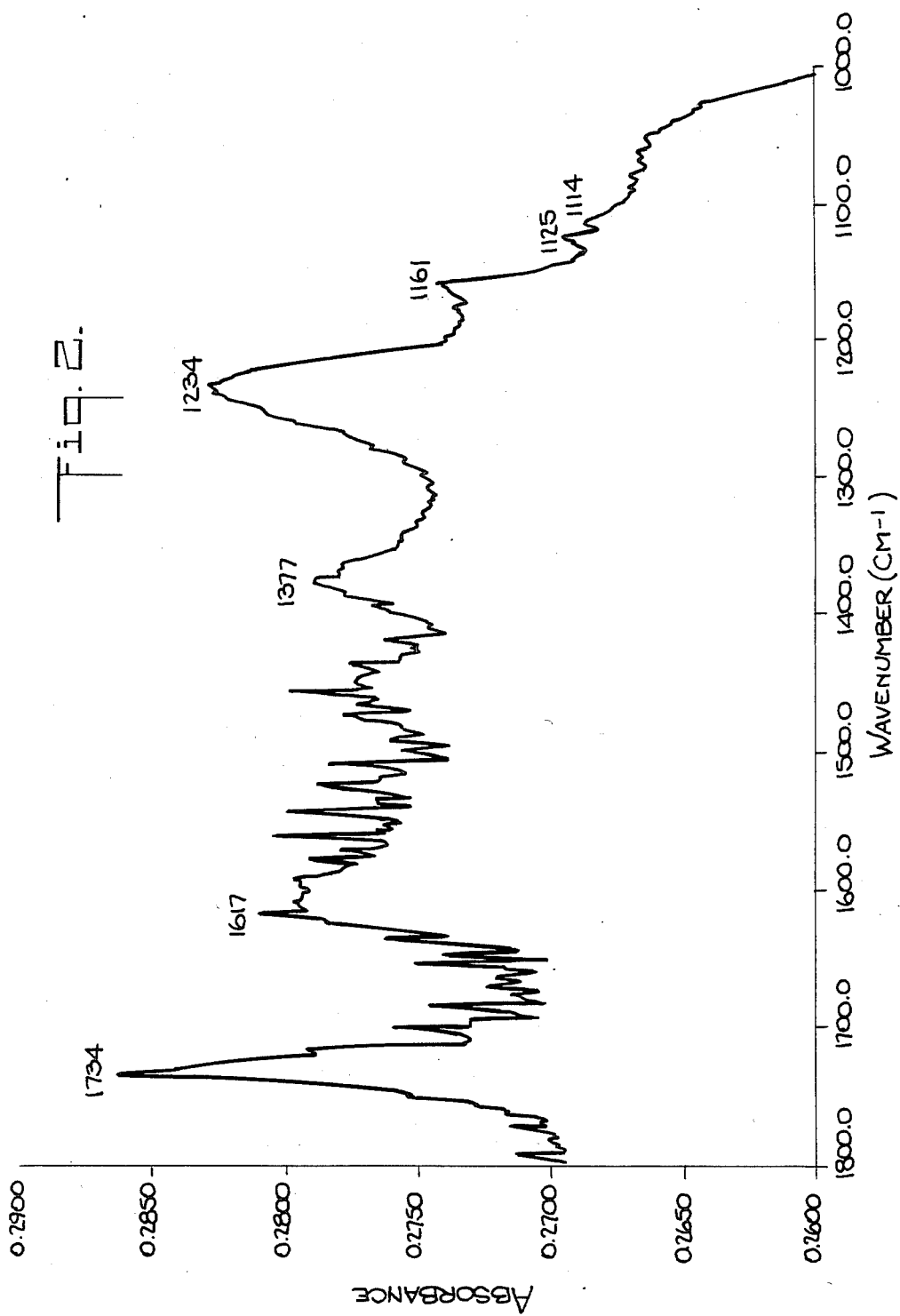
FIG. 2 is the infrared absorption spectrum for the photo-product coating of claim 22.

FIG. 2 shows the infrared absorption spectrum of one particular Reactant Mixture III photo-product coating after exposure to a mercury arc vapor lamp in the presence of air for approximately 9 hours. The reactant mixture contains 4.00% THBP, 76.75% ethanol, 4.00% deionized water, 8.00% alcohol, 1.00% triethanolamine, 0.5% acetic acid (99.9% concentration), 0.75% copper acetate, and 5.00% of a polymer consisting of 60% ethyl acrylate and 40% methylmethacrylate. The infrared absorption spectrum of FIG. 2 was determined by placing a silver chloride plate in the above mixture, and leaving the plate and reactant mixture exposed to the mercury arc vapor lamp for approximately 9 hours in a normal atmosphere. After exposure, the plate was removed, washed with ethanol, then washed with acetone, dried and placed into the FTIR.

The most preferred substrate embodiment of this invention consists of a natural or synthetic gemstone or mineral substrate having on its surface an adherent photo-product coating, which coating is formed by exposing to light in the presence of an oxygen source, a reactant mixture comprising (a) 2,2',4,4'-tetrahydroxybenzophenone; (b) ammonium hydroxide; (c) at least one metal salt; and (d) at least one amine; in a solvent. Additionally, the Reactant Mixture IV method of forming an adherent photo-product coating on the surface of a natural or synthetic gemstone or mineral substrate is within the scope of this invention.

The only benzophenone found that meets the objectives of this invention and provides a suitable photo-product coating is 2,2',4,4'-tetrahydroxybenzophenone. Additionally, sources of ammonium and hydroxyl ion, other than ammonium hydroxide, have not proven effective in producing a photo-product coating of this invention in Reactant Mixture IV.

The formulas of the reaction products of this invention are unknown. It is postulated that, in the first step of the process, the ammonium hydroxide deprotonates the hydroxyl group adjacent to the THBP carbonyl group. Under the influence of light and oxygen, the deprotonated THBP is thought to form a diradical and then form both a coordination complex with the metal cation and an addition product with another THBP molecule.

Typical concentrations of the reactants of Reactant Mixture IV are given in Table 1 below:

TABLE 1

| | Reactant Mixture IV Formulations | | |
| --- | --- | --- | --- |
| | Concentration | | |
| Ingredients | General | Preferred | Most Preferred |
| THBP | 0.01 to 10% | 3.0 to 5.0% | 4.0% |
| NH$_4$OH | | | |
| (28.5% conc.) | 0.1 to 10% | 0.25 to 1.75% | 1.0% |
| (100% conc.) | 0.1 to 1% | 0.1 to 0.5% | 0.3% |
| Metal salt | 0.001 to 5% | 0.05 to 0.5% | 0.2% |
| Amine | 0.001 to 2% | 0.25 to 1% | 0.6% |
| H$_2$O | 0 to 15% | 6 to 10% | 8.0% |
| Alcohol | balance to 100% | balance to 100% | balance to 100% |

The Method of Reactant Mixture IV is typically carried out as described above for the Methods of Reactant Mixture I and II. When the reactant mixture is contacted with a substrate, such as glass, and exposed to sunlight in the presence of oxygen, a visible photo-product coating is pooduced in a few hours, especially with the faster reacting metals, such as copper, manganese and iron. Exposure of this formulation to a mercury arc lamp in the presence of oxygen produces a visible photo-film within a few minutes.

Although applicants do not wish to be bound by any particular theory, the photo-ligand-metal-coordination complex of Reactant Mixture IV is believed to proceed as follows: THBP, preferably at least about 6 moles and more preferably at least about 18 moles, is mixed with at least 5 moles of ammonium hydroxide, in a suitable solvent, preferably an aqueous alcohol solvent, to form deprotonated THBP. The metal salt, preferably about 1 mole of a nickel salt is then mixed with 5 moles of an amine, preferably triethanolamine, to form a nickel salt-triethanolamine coordination complex. This complex is then mixed with the deprotonated THBP to form a metal-coordination complex that upon exposure to light in the presence of oxygen forms a photo-product of the present invention.

The photo-product coatings of this invention are insoluble in the reaction media and many other solvents, and therefore, are long lasting and durable. Once applied, the photo-product coatings cannot be removed without chemical treatment. To date, only strong solvents, such as dimethyl sulfoxide, appear to solubilize or form a complex with the photo-product coating to effect its removal. Additionally, dimethyl formamide will dissolve the coatings of Reactant Mixture I. It is known, however, that the photo-product coating will form water-soluble salts with appropriate bases. For example, the photo-film can be dissolved by any strong basic material, such as sodium, potassium or ammonium hydroxide, or mixtures thereof, at pH above 10. Typically, the film is solubilized at a pH from 10.2 to 10.5. The photo-product can be precipitated as a solid from these basic solutions by the addition of an acid, such as acetic acid, to lower the pH to below about 7.0. The pH ranges of Reactant Mixtures I, II and IV typically range from about 8.5 to 9.9.

The method of cleaning the natural and synthetic gemstone and mineral substrates of this invention involves the steps of forming an adherent photo-product coating on the surface of the substrate as described above for Methods of Reactant Mixture I-IV and then removing that photo-product coating from the surface of the substrate by a solvent or base material as described herein. The cleaning of substrates is critical, for example, when the substrate is used for semiconductor deposition.

percentages are weight precents based on the total weight of the composition.

The reactant mixtures of this invention also preferably employ various polymers, such as ethyl acrylate and/or methylmethacrylate, or other alcohol-soluble resin polymers, that act as a matrix so that the reactants can be easily applied to substrates such as windows, and thereby allow the formation of the photo-product on the substrate.

Figure 3:
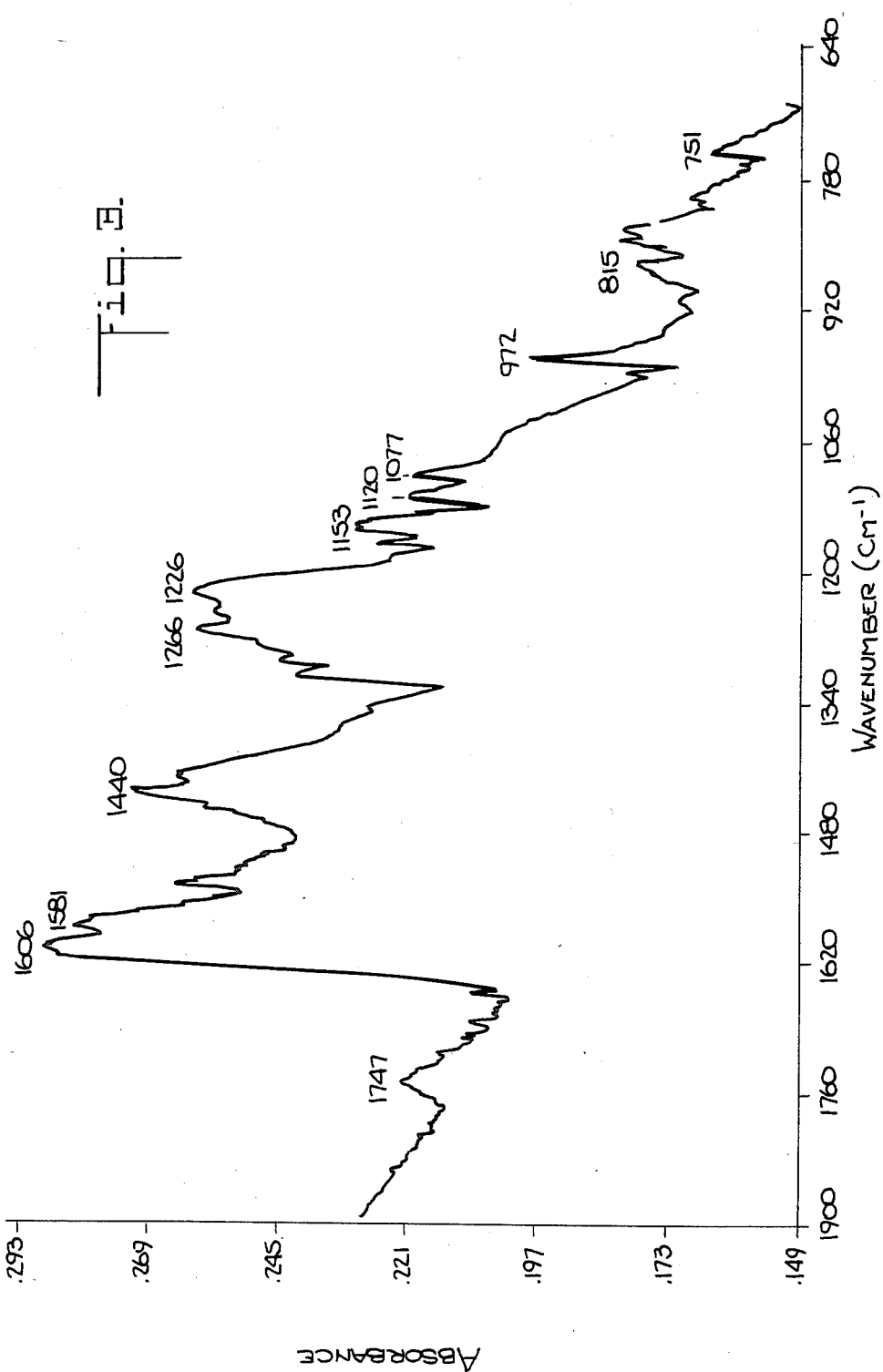
FIG. 3 is the infrared absorption spectrum for the photo-product coating of claim 23.

FIG. 3 shows the infrared absorption spectrum of one particular Reactant Mixture IV photo-product coating wherein the reactant mixture contained 4.14% THPP, 86.0% ethanol, 0.63% triethanolamine, 8.00% deionized water, 1.03% ammonium hydroxide (at 28.5% conc.) and 0.2% nickel chloride and was exposed to fluorescent light in the presence of oxygen for four days. The absorption spectrum was determined in the same manner as described for FIGS. 1 and 2.

In another aspect of this invention, the adherent photo-product coating functions as a prime coating thereby allowing the deposition or attachment of other materials to the substrates of this invention.

Other aspects and embodiments of this invention are shown in the following Examples which are illustrative of scope.

EXAMPLES 1-15

Examples 1-15 of Table 2 were prepared by contacting the ingredients shown in Table 2 and exposing them to light, either sunlight or artificially produced light, on window glass to provide photo-product coatings exhibiting reductions in both ultraviolet and infrared transmittance. These coatings typically vary in thickness from about 1000 to 3000 angstroms

TABLE 2

| EXAMPLES | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Reactant Mixture III Formulations | | | | | | | | | | | | | | | |
| Ethanol | 86.7 | 87.3 | 77.2 | 86.3 | 86.1 | 86.39 | 85.6 | 85.0 | 84.96 | 84.5 | 80.5 | 80.5 | 78.5 | 81.75 | 76.9 |
| Deionized Water | 8.0 | 8.0 | 8.0 | 8.0 | 8.0 | 8.2 | 8.1 | 8.0 | 7.99 | 8.0 | 8.0 | — | — | — | 4.0 |
| THBP | 4.0 | 4.0 | 4.0 | 4.0 | 4.0 | 3.94 | 4.0 | 4.5 | 4.59 | 4.5 | 4.0 | 2.0 | 3.5 | 4.0 | 4.0 |
| TEA | 0.5 | 0.6 | 0.6 | 1.0 | 1.0 | 1.1 | 1.07 | 1.0 | 1.1 | 1.0 | 1.0 | 1.0 | 1.0 | 1.0 | 1.0 |
| Metal Salt | 0.4[1] | 0.2[2] | 0.2[2] | 0.2[3] | 0.2[3] | 0.5[3] | 1.0[3] | 1.0[3] | 0.99[4] | 1.0[3] | 1.0[3] | 1.0[3] | 1.5[3] | 0.75[3] | 1.0[3] |
| Acetic Acid[a] | 0.4 | 0.1 | 10.0 | 0.5 | 0.5 | 0.54 | 0.54 | 0.5 | 0.65 | 0.5 | 0.5 | 0.5 | 0.5 | 0.5 | 1.0[g] |
| Stearyl[d] or benzyl[e] alcohol | — | — | — | — | 0.2[d] | — | — | — | — | — | 8.0[e] | 10.0[e] | 10.0[e] | 8.0[e] | 8.0 |
| Matrix Polymer | — | — | — | — | — | — | — | — | — | 0.5[b] | 5.0[c] | 5.0[c] | 5.0[c] | 4.0[c] | 5.0[c] |

[1] silver acetate
[2] $FeCl_2 \cdot 4H_2O$
[3] copper acetate
[4] zinc acetate
[a] 99.9% concentrated acetic acid
[b] Carbsoset 525 B. F. Goodrich
[c] 60% ethyl acrylate and 40% methylmethacrylate
[g] $CO_2$ gas The addition of iodine to the reactant mixtures of this invention has been found to further reduce the transmittance of ultraviolet and infrared radiation in accordance with the teachings of this invention. The iodine is mixed with the reactants prior to exposure to light to yield these beneficial results. The concentration of iodine that may be utilized varies from about 0.001% to about 5%, with a range of 0.01% to 1% being preferred. These

EXAMPLES 16-25

The Reactant Mixture IV formulas of Table 3 were also prepared by contacting the ingredients shown and exposing them to light, either sunlight or artificially produced light, on window glass to provide photo-product coatings which significantly reduced the transmission of infrared and ultraviolet radiation.

TABLE 3

| EXAMPLES | Reactant Mixture IV Formulations | | | | | | | | | |
|---|---|---|---|---|---|---|---|---|---|---|
| | 16 | 17 | 18 | 19 | 20 | 21 | 22 | 23 | 24 | 25 |
| Ethanol | 86.0 | 87.4 | 90.85 | 86.0 | 86.0[a] | 86.1 | 95.4 | 86.1 | 86.2 | 86.2 |
| THBP | 4.0 | 2.0 | 3.0 | 4.14 | 4.14 | 4.0 | 2.0 | 4.0 | 4.0 | 4.0 |
| TEA | 0.5 | 0.5 | 0.75 | 0.63 | 0.63 | 0.5 | 0.5 | 0.5 | 0.6 | 0.6 |
| NH$_4$OH (28.5%) | 1.0 | 1.0 | 5.0 | 1.03 | 1.03 | 1.0 | 1.0 | 1.0 | 1.0 | 1.0 |
| Deionized Water | 8.0 | 8.0 | — | 8.0 | 8.0 | 8.0 | — | 8.0 | 8.0 | 8.0 |
| Metal Salt | 0.5[1] | 0.1[1] | 0.4[1] | 0.2[1] | 0.2[1] | 0.4[2] | 0.1[3] | 0.4[4] | 0.2[5] | 0.2[6][7] |
| Benzyl Alcohol | 1.0 | — | — | — | — | — | 1.0 | — | — | — |

[1] NiCl$_2$.H$_2$O
[2] silver acetate
[3] iron chloride (FeCl$_2$.H$_2$O)
[4] copper acetate monohydrate
[5] MnCl$_2$.4H$_2$O
[6] ZnCl$_2$
[7] CuCl$_2$.H$_2$O
[a] isopropanol

EXAMPLE 26

A particular Reactant Mixture IV composition was prepared by contacting 4.14% THBP, 0.63% triethanolamine, 1.03% ammonium hydroxide (28.5% conc.), 0.2% of NiCl$_2$.6H$_2$O, 8.0% deionized water, and 86.0% ethanol in a glass vial, and then exposing this mixture to light in the presence of oxygen. Glass vials coated with the photo-product were then rinsed with 100 ml of distilled water containing 4 grams of 28 5% sodium hydroxide in order to remove the photo-compound from the sides of the container. A salt solution of this photo-compound was then precipitated with acetic acid, centrifuged and washed with distilled water and absolute alcohol and dried. The elemental analysis showed 47.71% carbon, 3.72% hydrogen, 5.54% nitrogen, 2.3% nickel and 12.23% residue.

EXAMPLE 27

A typical Reactant Mixture IV composition containing iodine was prepared by contacting 4.0% THBP, 86.1% ethanol, 0.1% iodine (99.9% conc.), 0.6% triethanolamine, 8.0% deionized water, 1.0% ammonium hydroxide (28.5% conc.), and 0.2% copper acetate, or nickel chloride; and then exposing this mixture while in contact with a suitable substrate such as glass, to light in the presence of oxygen.

EXAMPLE 28

Example 28 was prepared by cleaning the gemstone substrates, ruby, peridot, diamond, emerald and zircon, in acetone, placing them in a petri dish, and covering them with a reactant mixture consisting of: 4.0% THBP, 84.3% ethanol, 0.6% triethanolamine, 10.0% deionized water, 1.0% ammonium hydroxide (28.5% conc.), and 0.1% lead chloride (PbCl$_2$). Since lead chloride goes into the solution very slowly, heating with agitation is recommended, along with increasing the concentration of water. The reactant mixture in contact with the above-mentioned substrate was left on a laboratory window sill in direct sunlight for about 6 hours, at the same time being exposed to the fluorescent light in the laboratory, after which the gemstone substrates were removed from the solution, washed with ethanol and acetone and air dried.

In each case the photo-product coating adhered tenaciously to the surface of the gemstone substrate and changed their aesthetics, as evidenced by the following color changes: ruby (became redder), peridot (yellow/green to brown), diamond (clear to pink), emerald (green to black/green), and zircon (clear to pink).

EXAMPLES 29-30

In Examples 29-30, both polished quartz and polished sapphire substrates were each separately exposed to the following two reactant mixtures in the presence of sunlight for approximately 12 hours, and at the same time eeing exposed to the fluorescent light in the laboratory, to form an adherent photo-product coating on their surfaces. The first reactant mixture consisted of 4.0% THBP, 85.2% ethanol, 1.0% iodine (99.9% conc.), 0.6% triethanolamine, 8.0% deionized water, 1.0% ammonium hydroxide (28.5% conc.), and 0.2% copper acetate. The second reactant mixture consisted of 4.0% THBP, 84.3% ethanol, 0.6% triethanolamine, 10.0% deionized water, 1.0% ammonium hydroxide (28.5% conc.), and 0.1% lead chloride. These coatings are useful as sensors and detectors to block or pass radiation of selected frequencies. Additionally, if the substrate is used as a semiconductor, the photo-product coating not only protects it from the elements, but also may be used to dope the semiconductor substrate with various materials including halogens such as iodine, bromine, chlorine and fluorine.

EXAMPLE 31

In Example 31, zircon, garnet and diamond were each separately exposed to the following reactant mixture in the presence of light and atmospheric oxygen to form an adherent photo-product coating on their surfaces. The reactant mixture consisted of 4.14% THBP, 86.0% ethanol, 0.63% triethanolamine, 8.0% deionized water, 1.03% ammonium hydroxide (28.5% conc.), and 0.2% nickel chloride (NiCl$_2$.6H$_2$O). These substrates were exposed to sunlight for two hours in a petri dish containing the reactant mixture while at the same time being exposed to the fluorescent light in the laboratory. After exposure the substrates were removed from the reactant mixture, washed with ethanol, followed by acetone and blow dried. With the photo-product coatings, the zircon and diamond both had a blue hue, and the garnet was browner and darker red in color.

EXAMPLE 32

In Example 32, polished quartz was exposed for 3 hours to the following reactant mixture and an 85 watt medium pressure mercury arc lamp (Gates Lamp MLA 85) positioned 3 inches above the petri dish containing the reactant mixture and the polished quartz. The reactant mixture consisted of 4.0% THBP, 84.3% ethanol, 0.6% triethanolamine, 10.0% deionized water, 1.0% ammonium hydroxide (28.5% conc.), and 0.1% lead chloride. After exposure, a pink coating approximately 2000 Angstroms in thickness was observed on the quartz substrate.

What is claimed is:

1. A natural or synthetic gemstone substrate or mineral substrate having on its surface an adherent photo-product coating, which coating is formed by exposing to light in the presence of an oxygen source, a reactant mixture having a pH from about 7 to 10.5 comprising:
   (a) 2,2',4,4'-tetrahydroxybenzophenone;
   (b) ammonium hydroxide; and
   (c) optionally a trace amount of at least one reactive metal selected from the group consisting of zinc, copper, nickel, silver, iron, manganese, lead, cobalt, zirconium, mercury, palladium, cadmium, ruthenium, rhodim, and mixtures thereof; in a solvent.

2. A natural or synthetic gemstone substrate having on its surface an adherent photo-product coating, which coating is formed by exposing to light in the presence of an oxygen source, a reactant mixture having a pH from about 7,to 10.5 comprising:
   (a) 2,2',4,4'-tetrahydroxybenzophenone;
   (b) ammonium hydroxide; and
   (c) optionally a trace amount of at least one reactive metal selected from the group consisting of zinc, copper, nickel, silver, iron, manganese, lead, cobalt, zirconium, mercury, palladium, cadmium, ruthenium, rhodium, and mixtures thereof; in a solvent.

3. A natural or snythetic mineral substrate having on its surface an adherent photo-product coating, which coating is formed by exposing to light in the presence of an oxygen source, a reactant mixture having a pH from about 7 to 10.5 comprising:
   (a) 2,2'4,4'-tetrahydroxybenzophenone;
   (b) ammonium hydroxide; and
   (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; in a solvent.

4. A natural or synthetic gemstone substrate having on its surface an adherent photo-product coating, which coating is formed by exposing to light in the presence of an oxygen source, a reactant mixture having a pH from about 7 to 10.5 comprising:
   (a) 2,2'4,4'-tetrahydroxybenzophenone;
   (b) ammonium hydroxide; and
   (c) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; in a solvent.

5. A natural or synthetic mineral substrate having on its surface an adherent photo-product coating, which coating is formed by exposing to light in the presence of an oxygen source, a reactant mixture having a pH from about 7 to 10.5 comprising:
   (a) 2,2'4,4'-tetrahydroxybenzophenone;
   (b) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; add
   (c) at least one amine; in a solvent.

6. A natural or synthetic gemstone substrate having on its surface an adherent photo-product coating, which coating is formed by exposing to light in the presence of an oxygen source, a reactant mixture having a pH from about 7 to 10.5 comprising:
   (a) 2,2'4,4'-tetrahydroxybenzophenone;
   (b) at least one metal salt wherein the metal is selected from the group consisting of zinc, copper, nickel, silver, iron, manganese, lead, cobalt, zirconium, mercury, palladium, cadmium, ruthenium, rhodium, and mixtures thereof; and
   (c) at least one amine; in a solvent.

7. A natural or synthetic mineral substrate having on its surface an adherent photo-product coating, which coating is formed by exposing to light in the presence of an oxygen source, a reactant mixture having a pH from about 7 to 10.5 comprising:
   (a) 2,2'4,4'-tetrahydroxybenzophenone;
   (b) ammonium hydroxide;
   (c) at least one metal salt wherein the metal is selected from the group consisting of zinc, copper, nickel, silver, iron, manganese, lead, cobalt, zirconium, mercury, palladium, cadium, ruthenium, rhodium, and mixtures thereof; and
   (d) at least one amine; in a solvent.

8. A natural or synthetic gemstone substrate having on its surface an adherent photo-product coating, which coating is formed by exposing to light in the presence of an oxygen source, a reactant mixture having a pH from about 7 to 10.5 comprising:
   (a) 2,2'4,4'-tetrahydroxybenzophenone;
   (b) ammonium hydroxide;
   (c) at least one metal salt wherein the metal is selected from the group consisting of zinc, copper, nickel, silver, iron, manganese, lead, cobalt, zirconium, mercury, palladium, cadium, ruthenium, rhodium, and mixtures thereof; and
   (d) at least one amine; in a solvent.

9. The substrate of claims 3, 4, 5, 6, 7 or 8 wherein the anion of the metal salt is selected from the group consisting of sulfate, nitrate, bromide, chloride, acetate, formate, carbonate, benzenesulfonate, benzoate and mixtures thereof.

10. The substrate of claims 3, 4, 5, 6, 7 or 8 wherein the metal salt is selected from the group consisting of nickel chloride, cobalt chloride, silver acetate, iron chloride copper acetate, lead chloride, zinc acetate, copper chloride and mixtures thereof.

11. The substrate of claims 1, 2, 3, 4, 5, 6, 7 or 8 wherein the solvent is selected from the group consisting of ethanol, isopropanol, n-propanol, isobutanol, n-butanol, mixtures and aqueous mixtures thereof.

12. The substrate of claims 5, 6, 7 or 8 wherein the amine is selected from the group consisting of triethanolamine, diethanolamine, ethanolamine, monomethanolamine, butylamine, n-amylamine and mixtures thereof.

13. The substrate of claims 1, 2, 3, 4, 5, 6, 7 or 8 wherein the reactant mixture further comprises at least one of iodine, bromine, chlorine and fluorine as a dopant.

14. The mineral substrate of claims 1, 3, 5 or 7 which is selected from the group consisting of glass, quartz and gallium arsenide.

15. The gemstone substrate of claims 2, 4, 6 or 8 which is selected from the group consisting of sapphire, ruby, peridot, diamond, emerald, zircon and garnet.

16. A natural or synthetic mineral substrate having on its surface an adherent photo-product coating, which coating is formed by exposing to light in the presence of an oxygen source, a reactant mixture having a pH from about 7 to 10.5 comprising:
   (a) 2,2',4,4'-tetrahydroxybenzophenone;
   (b) ammonium hydroxide;
   (c) lead chloride; and
   (d) triethanolamine; in a solvent.

17. A natural or synthetic gemstone substrate having on its surface an adherent photo-product coating, which coating as formed by exposing to light in the presence of an oxygen source, a reactant mixture having a pH from about 7 to 10.5 comprising:
   (a) 2,2',4,4'-tetrahydroxybenzophenone;
   (b) ammonium hydroxide;
   (c) lead chloride; and
   (d) triethanolamine; in a solvent.

18. A natural or synthetic mineral substrate having on its surface an adherent photo-product coating, which coating is formed by exposing to light in the presence of an oxygen source, a reactant mixture having a pH from about 7 to 10.5 comprising:
   (a) 2,2',4,4'-tetrahydroxybenzophenone;
   (b) ammonium hydroxide;
   (c) copper acetate;
   (d) triethanolamine; and
   (e) iodine; in a solvent.

19. A natural or synthetic gemstone substrate having on its surface an adherent photo-product coating, which coating is formed by exposing to light in the presence of an oxygen source, a reactant mixture having a pH from about 7 to 10.5 comprising:
   (a) 2,2',4,4'-tetrahydroxybenzophenone;
   (b) ammonium hydroxide;
   (c) copper acetate;
   (d) triethanolamine; and
   (e) iodine; in a solvent.

20. A glass substrate having on its surface an adherent photo-product coating suitable for reducing electromagnetic radiation in the infrared and ultraviolet range, containing the elements carbon, hydrogen, oxygen, nitrogen and a trace amount of zinc, and exhibiting characteristic absorption peaks in the infrared region of the spectrum, when cast as a film on a silver chloride plate at the following frequencies expressed in reciprocal centimeters: 1616, 1543, 1517, 1463, 1400, 1367, 1233, 1191, 1106, 996, 977, 845 and 805; formed by exposing to light in the presence of an oxygen source, a reactant mixture comprising: 2,2',4,4'-tetrahydroxybenzophenone, ammonium hydroxide and a trace amount of zinc.

21. A glasss substrate having on its surface an adherent photo-product coating suitable for reducing electromagnetic radiation in the infrared and ultraviolet range, containing the elements carbon, hydrogen, nitrogen, oxygen and copper, and exhibiting characteristic absorption peaks in the infrared region of the spectrum, when cast as a film on a silver chloride plate at the following frequencies expressed in reciprocal centimeters: 1734, 1617, 1377, 1234, 1161, 1125, and 1114; formed by exposing to light in the presence of an oxygen source, a reactant mixture comprising: 2,2'4,4'-tetrahydroxybenzophenone, triethanolamine and copper cation.

22. A glass substrate having on its surface an adherent photo-product coating suitable for reducing electromagnetic radiation in the infrared and ultra-violet range, containing the elements carbon, hydrogen, nitrogen, oxygen and nickel; exhibiting characteristic absorption peaks in the infrared region of the spectrum, when cast as a film on a silver chloride plate, at the following frequencies expressed in reciprocal centimeters: 1747, 1606, 1581, 1440, 1266, 1226, 1153, 1120, 1097, 972, 875, and 751; formed by exposing to light in the presence of an oxygen source a reactant mixture comprising: 2,2',4,4'-tetrahydroxybenzophenone, triethanolamine, ammonium hydroxide and nickel cation.

23. A method of forming an adherent photo-product coating on the surface of a natural or synthetic gemstone substrate or mineral substrate comprising the steps of:
   (1) preparing the reactant mixture of claim 1;
   (2) contacting said substrate with said reactant mixture; and
   (3) exposing said reactant mixture in contact with said substrate to light in the presence of an oxygen source.

24. A method of forming an adherent photo-product coating on the surface of a natural or synthetic gemstone substrate comprising the steps of:
   (1) preparing a reactant mixture of claim 2;
   (2) contacting said substrate with said reactant mixture; and
   (3) exposing said reactant mixture in contact with said substrate to light in the presence of an oxygen source.

25. A method of forming an adherent photo-product coating on the surface of a natural or synthetic mineral substrate comprising the steps of:
   (1) preparing a reactant mixture of claim 3;
   (2) contacting said substrate with said reactant mixture; and
   (3) exposing said reactant mixture in contact with said substrate to light in the presence of an oxygen source.

26. A method of forming an adherent photo-product coating on the surface of a natural or synthetic gemstone substrate comprising the steps of:
   (1) preparing a reactant mixture of claim 4;
   (2) contacting said substrate with said reactant mixture; and
   (3) exposing said reactant mixture in contact with said substrate to light in the presence of an oxygen source.

27. A method of forming an adherent photo-product coating on the surface of a natural or synthetic mineral substrate comprising the steps of:
   (1) preparing a reactant mixture of claim 5;
   (2) contacting said substrate with said reactant mixture; and
   (3) exposing said reactant mixture in contact with said substrate to light in the presence of an oxygen source.

28. A method of forming an adherent photo-product coating on the surface of a natural or synthetic gemstone substrate comprising the steps of:
   (1) preparing a reactant mixture of claim 6;
   (2) contacting said substrate with said reactant mixture; and
   (3) exposing said reactant mixture in contact with said substrate to light in the presence of an oxygen source.

29. A method of forming an adherent photo-product coating on the surface of a natural or synthetic mineral substrate comprising the steps of:
(1) preparing a reactant mixture of claim 7;
(2) contacting said substrate with said reactant mixture; and
(3) exposing said reactant mixture in contact with said substrate to light in the presence of an oxygen source.

30. A method of forming an adherent photo-product coating on the surface of a natural or synthetic gemstone substrate comprising the steps of:
(1) preparing a reactant mixture of claim 8;
(2) contacting said substrate with said reactant mixture; and
(3) exposing said reactant mixture in contact with said substrate to light in the presence of an oxygen source.

31. The method of claims 25, 26, 27, 28, 29 or 30 wherein the anion of the metal salt is selected from the group consisting of sulfate, nitrate, bromide, chloride, acetate, formate, carbonate, benzenesulfonate, benzoate and mixtures thereof.

32. The method of claims 25, 26, 27, 28, 29 or 30 wherein the metal salt is selected from the group consisting of nickel chloride, cobalt chloride, silver acetate, iron chloride, copper acetate, lead chloride, zinc acetate, copper chloride and mixtures thereof.

33. The method of claims 23, 24, 25, 26, 27, 28, 29 or 30 wherein the solvent is selected from the group consisting of ethanol, isopropanol, n-propanol, isobutanol, n-butanol, mixtures and aqueous mixtures thereof.

34. The method of claims 27, 28, 29 or 30 wherein the amine is selected from the group consisting of triethanolamine, diethanolamine, ethanolamine, monomethanolamine, butylamine, n-amylamine and mixtures thereof.

35. The method of claims 23, 24, 25, 26, 27, 28, 29 or 30 wherein the reactant mixture further comprises at least one of iodine, bromine, chlorine or fluorine as a dopant.

36. The method of claims 23, 25, 27 or 29 wherein said mineral substrate is selected from the group consisting of glass, quartz and gallium arsenide.

37. The method of claims 24, 26, 28 or 30 wherein said gemstone substrate is selected from the group consisting of sapphire, ruby, peridot, diamond, emerald, zircon and garnet.

38. A method of cleaning a natural or synthetic mineral substrate comprising the steps of:
(A) forming an adherent photo-product coating on the surface of said substrate by:
(1) preparing a reactant mixture of claim 1;
(2) contacting said substrate with said reactant mixture; and
(3) exposing said reactant mixture in contact with said substrate to light in the presence of an oxygen source; and
(B) removing said photo-product coating from the surface of said substrate.

39. A method of cleaning a natural or synthetic gemstone substrate comprising the steps of:
(A) forming an adherent photo-product coating on the surface of said substrate by:
(1) preparing a reactant mixture of claim 2;
(2) contacting said substrate with said reactant mixture; and
(3) exposing said reactant mixture in contact with said substrate to light in the presence of an oxygen source; and
(B) removing said photo-product coating from the surface of said substrate.

40. A method of cleaning a natural or synthetic mineral substrate comprising the steps of:
(A) forming an adherent photo product coating on the surface of said substrate by:
(1) preparing a reactant mixture of claim 3;
(2) contacting said substrate with said reactant mixture; and
(3) exposing said reactant mixture in contact with said substrate to light in the presence of an oxygen source; and
(B) removing said photo-product coating from the surface of said substrate.

41. A method of cleaning a natural or synthetic gemstone substrate comprising the steps of:
(A) forming an adherent photo-product coating on the surface of said substrate by:
(1) preparing a reactant mixture of claim 4;
(2) contacting said substrate with said reactant mixture; and
(3) exoosing said reactant mixture in contact with said substrate to light in th presence of an oxygen source; and
(B) removing said photo-product coating from the surface of said substrate.

42. A method of cleaning a natural or synthetic mineral substrate comprising the steps of:
(A) forming an adherent photo-product coating on the surface of said substrate by:
(1) preparing a reactant mixture of claim 5;
(2) contacting said substrate with said reactant mixture; and
(3) exposing said reactant mixture in contact with said substrate to light in the presence of an oxygen source; and
(B) removing said photo-product coating from the surface of said substrate.

43. A method of cleaning a natural or synthetic gemstone substrate comprising the steps of:
(A) forming an adherent photo-product coating on the surfcce of said substrate by:
(1) preparing a reactant mixture of claim 6;
(2) contacting said substrate with said reactant mixture; and
(3) exposing said reactant mixture in contact with said substrate to light in the presence of an oxygen source; and
(B) removing said photo-product coating from the surface of said substrate.

44. A method of cleaning a natural or synthetic mineral substrate comprising the steps of:
(A) forming an adherent photo-product coating on the surface of said substrate by:
(1) preparing a reactant mixture of claim 7;
(2) contacting said substrate with said reactant mixture; and
(3) exposing said reactant mixture in contact with said substrate to light in the presence of an oxygen source; and
(B) removing said photo-product coating from the surface of said substrate.

45. A method of cleaning a natural or synthetic gemstone substrate comprising the steps of:

(A) forming an adherent photo product coating on the surface of said substrate by:
 (1) preparing a reactant mixture of claim 8;
 (2) contacting said substrate with said reactant mixture; and
 (3) exposing said reactant mixture in contact with said substrate to light in hhe presence of an oxygen source; and
(B) removing said photo-product coating from the surface of said substrate.

46. The method of cleaning of claims 38, 39, 40, 41, 42, 43, 44 or 45 wherein the photo product coating is removed by contact with a basic material.

47. The method of cleaning of claims 38, 39, 40, 41, 42, 43, 44 or 45 wherein the photo-product coating is removed by contact with a solvent.

48. The method of cleaning of claim 46 wherein the basic material is selected from the group consisting of sodium hydroxide, potassium hydroxide and ammonium hydroxide.

49. The method of cleaning of claim 47 wherein the solvent is dimethyl sulfoxide.

50. The method of cleaning of claims 38 or 39 wherein the photo-product coating is removed by contact with dimethyl formamide.

51. A natural or synthetic mineral substrate having on its surface an adherent photo-product coating, which coating is formed by exposing to light in the presence of an oxygen source, a reactant mixture having a pH from about 7 to 10.5 comprising:
 (a) 2,2',4,4'-tetrahydroxybenzophenone;
 (b) ammonium hydroxide; and
 (c) optionally a trace amount of at least one reactive metal selected fromthe group consisting of zinc, copper, nickel, silver, iron, manganese, lead, tin, cobalt, zirconium, mercury, palladium, cadium, ruthenium, rhodium, and mixtures thereof;
in a solvent.

52. A method of forming an adherent photo-product coating on the surface of a natural or synthetic mineral substrate comprising the steps of:
 (1) preparing the reactant mixture of claim 1;
 (2) contacting said substrate with said reactant mixture; and
 (3) exposing said reactant mixture in contact with said substrate to light in the presence of an oxygen source.

* * * * *